(12) United States Patent
Laboureau et al.

(10) Patent No.: US 9,827,311 B2
(45) Date of Patent: *Nov. 28, 2017

(54) COMBINATION OF A LIGHT RAY WITH A CYTOCHROME C OXIDASE SUBSTRATE PARTICULARLY FOR IMPROVING THE APPEARANCE OF THE SKIN AND/OR HAIR

(71) Applicant: L'OREAL, Paris (FR)

(72) Inventors: Julien Laboureau, Paris (FR); Quang Lan Nguyen, Antony (FR); Dang-Man Pham, Sucy-en-Brie (FR)

(73) Assignee: L'OREAL, Paris (FR)

( * ) Notice: Subject to any disclaimer, the term of this patent is extended or adjusted under 35 U.S.C. 154(b) by 145 days.

This patent is subject to a terminal disclaimer.

(21) Appl. No.: 14/802,616

(22) Filed: Jul. 17, 2015

(65) Prior Publication Data
US 2016/0015812 A1    Jan. 21, 2016

Related U.S. Application Data

(63) Continuation of application No. 12/866,575, filed as application No. PCT/FR2009/050193 on Feb. 6, 2009, now Pat. No. 9,119,798.
(Continued)

(30) Foreign Application Priority Data

Feb. 6, 2008 (FR) ...................... 08 50758

(51) Int. Cl.
*A61K 8/66* (2006.01)
*A61N 5/06* (2006.01)
(Continued)

(52) U.S. Cl.
CPC ............... *A61K 41/00* (2013.01); *A61K 8/19* (2013.01); *A61K 8/494* (2013.01); *A61K 8/66* (2013.01);
(Continued)

(58) Field of Classification Search
CPC ...... A61K 8/19; A61K 8/494; A61K 2800/81; A61K 2800/92; A61Q 7/00; A61N 5/0617; A61N 5/062
See application file for complete search history.

(56) References Cited

U.S. PATENT DOCUMENTS 5,853,728 A    12/1998 Tanabe et al.
2003/0023283 A1    1/2003 McDaniel
(Continued)

FOREIGN PATENT DOCUMENTS

JP    2003-12487    1/2003
JP    2005-503388    2/2005
(Continued)

OTHER PUBLICATIONS

Perrin, A. et al., "A New Cytochrome C-Inducing Active Ingredient That Enhances Mitochondrial Membrane Potential and Functioning", Journal of Investigative Dermatology, vol. 127, No. 418, p. S70, (2007) XP002497798.
(Continued)

*Primary Examiner* — Nathan J Jenness
(74) *Attorney, Agent, or Firm* — Oblon, McClelland, Maier & Neustadt, L.L.P.

(57) ABSTRACT

The present invention relates more specifically to a cosmetic treatment method intended in particular to improve the appearance of the skin and/or hair comprising the simultaneous and/or sequential administration:
a) of at least one cytochrome C oxidase substrate and/or of at least one agent which increases the expression of the said substrate; and
b) of at least one light radiation exhibiting at least one predominant wavelength which activates cytochrome C oxidase.
In particular, the said light radiation exhibits at least one predominant wavelength which activates cytochrome C oxi-
(Continued)

dase ranging from 550 to 1000 nm, in particular from 550 to 800 nm, preferably from 620 to 700 nm and more preferably still from 640 to 680 nm and is preferably used at a dose ranging from 0.01 to 200 $J/cm^2$, preferably from 0.1 to 30 $J/cm^2$, more preferably from 1 to 30 $J/cm^2$, indeed even from 5 to 30 $J/cm^2$.

The invention also relates to a composition comprising at least one cytochrome C oxidase substrate and/or one agent which increases the expression of the said substrate and at least one compound emitting and/or filtering, in particular under exposure to light, a light radiation exhibiting at least one predominant wavelength which activates cytochrome C oxidase, and to a kit comprising at least one composition comprising at least one cytochrome C oxidase substrate and/or one agent which increases the expression of the said substrate and one device and/or one compound emitting/filtering a light radiation exhibiting at least one predominant wavelength which activates cytochrome C oxidase.

15 Claims, 2 Drawing Sheets

Related U.S. Application Data (60) Provisional application No. 61/027,839, filed on Feb. 12, 2008.

(51) Int. Cl.
| | | |
|---|---|---|
| *A61K 41/00* | (2006.01) | |
| *A61K 8/19* | (2006.01) | |
| *A61K 8/49* | (2006.01) | |
| *A61Q 7/00* | (2006.01) | |
| *A61Q 19/00* | (2006.01) | |
| *A61Q 19/02* | (2006.01) | |
| *A61Q 19/08* | (2006.01) | |
| *A61K 38/17* | (2006.01) | |
| *A61K 45/06* | (2006.01) | |

(52) U.S. Cl.
CPC .......... *A61K 38/1709* (2013.01); *A61K 45/06* (2013.01); *A61Q 7/00* (2013.01); *A61Q 19/007* (2013.01); *A61Q 19/02* (2013.01); *A61Q 19/08* (2013.01); *A61K 2800/81* (2013.01); *A61K 2800/92* (2013.01); *A61N 5/0617* (2013.01); *C12Y 109/03001* (2013.01)

(56) References Cited

U.S. PATENT DOCUMENTS

| | | |
|---|---|---|
| 2005/0149150 A1 | 7/2005 | McDaniel |
| 2005/0186290 A1 | 8/2005 | Cals-Grierson |
| 2005/0203495 A1* | 9/2005 | Malak ............. A61B 18/203 606/9 |
| 2006/0129209 A1 | 6/2006 | McDaniel |
| 2006/0217690 A1 | 9/2006 | Bastin et al. |
| 2007/0184003 A1 | 8/2007 | Gaunitz |
| 2008/0033412 A1 | 2/2008 | Whelan et al. |
| 2009/0053748 A1 | 2/2009 | Stubbs et al. |

FOREIGN PATENT DOCUMENTS

| | | |
|---|---|---|
| WO | WO03/017824 | 3/2003 |
| WO | WO03/039478 | 5/2003 |
| WO | WO2005/011606 | 2/2005 |
| WO | WO2005/058960 | 6/2005 |

OTHER PUBLICATIONS

Bauza, E. et al., "A New Active Ingredient That Improves Skin Defense and Protection by Enhancing Mitochondrial Cytochrome C Expression", Journal of Investigative Dermatology, vol. 127 No. 419, p. S70 (2007) XP002497799.
Cazares-Delgadillo, et al., "Transdermal Delivery of Cytochrome C-A 12.4 kDa Protein-Across intact Skin by Constant-Current Iontophoresis", Pharmaceutical Research, vol. 24, No. 7, Jul. 7, 2007, pp. 1360-1368.
Hamblin et al. "Mechanisms of Low Level Light Therapy" Proc. SPIE 6140, Mechanisms for Low-Light Therapy, 614001 (Feb. 10, 2006).
Decision on Rejection in corresponding Japanese application No. 2010-545537, dated Dec. 11, 2014.
Comments on Decision on Rejection in corresponding Japanese application No. 2010-545537, dated Jan. 30, 2015.
G.S. Fedoseyeva, T.I. Karu, T.S. Lyapunova, N.A. Pomoshnikova, M.N. Meissel. The activation of yeast metabolism with He—Ne laser-II. Activity of enzymes of oxidative and phosphorus metabolism. Lasers Life Sci., 2 (1988), pp. 147-154.
Paulo C.L. Silveira, Emilio L. Streck, Ricardo A. Pinho, Evaluation of mitochondrial respiratory chain activity in wound healing by U low-level laser therapy, Journal of Photochemistry and Photobiology B: Biology, vol. 86, Issue 3, Mar. 1, 2007, pp. 279-282, ISSN 1011-1344, http://dx.doi.org/1 0.1 016/j.jphotobiol.2006.1 0.002.
Mahmoud et al. "Effects of Visible Light on the Skin" Photochemistry and Photobiology vol. 84 Is. 2, 450-462 (Jan. 31, 2008).
Bernstein "Hair Growth Induced by Diode Laser Treatment" Dermatologic Surgery vol. 31 Is. 5, 584-586 (2005).
Office Action issued Oct. 22, 2013 in Japanese Patent Application No. 2010-545537 (with English language translation).
Tiina Karu, "Photobiology of Low-Power Laser Effects" Health Physics, vol. 56, No. 5, May 1989, pp. 691-704.

* cited by examiner

COMBINATION OF A LIGHT RAY WITH A CYTOCHROME C OXIDASE SUBSTRATE PARTICULARLY FOR IMPROVING THE APPEARANCE OF THE SKIN AND/OR HAIR

This application is a Continuation of U.S. application Ser. No. 12/866,575, filed Nov. 9, 2010, now U.S. Pat. No. 9,119,798, which is a National Stage of International Application No. PCT/FR2009/050193, filed on Feb. 6, 2009, which claims benefit of U.S. Provisional application Ser. No. 61/027,839, filed on Feb. 12, 2008.

The present invention relates to the field of the care of the skin and/or hair and in particular of the improvement in the appearance of the skin and/or hair by light radiation.

The term "skin" is understood to mean the skin of the face and/or of the body, and also the scalp.

The present invention relates more specifically to a cosmetic treatment method intended in particular to improve the appearance of the skin and/or hair comprising the simultaneous and/or sequential administration:

of at least one cytochrome C oxidase substrate and/or of at least one agent which increases the expression of the said substrate; and of at least one light radiation exhibiting at least one predominant wavelength which activates cytochrome C oxidase.

The cosmetic treatment method according to the present invention comprises in particular the simultaneous and/or sequential administration, to a subject, in particular to a subject with healthy skin:

of at least one cytochrome C oxidase substrate and/or of at least one agent which increases the expression of the said substrate; and of at least one light radiation exhibiting at least one predominant wavelength which activates cytochrome C oxidase.

The term "healthy skin" is understood to mean skin not exhibiting an injury and/or infection.

In particular, the said light radiation according to the invention exhibits (emits) at least one predominant wavelength which activates cytochrome C oxidase ranging from 550 to 1000 nm (red and infrared emission spectrum), in particular from 550 to 800 nm, preferably from 620 to 700 nm and more preferably still from 640 to 680 nm, and is preferably used at a dose ranging from 0.01 to 200 $J/cm^2$, preferably from 0.1 to 30 $J/cm^2$, more preferably from 1 to 30 $J/cm^2$, indeed even from 5 to 30 $J/cm^2$.

The invention also relates to a composition comprising at least one cytochrome C oxidase substrate and/or one agent which increases the expression of the said substrate and at least one compound exhibiting and/or filtering, in particular under exposure to light, a light radiation exhibiting at least one predominant wavelength which activates cytochrome C oxidase, and also to a kit comprising at least one composition comprising at least one cytochrome C oxidase substrate and/or one agent which increases the expression of the said substrate and a device and/or a compound which emits/filters a light radiation exhibiting at least one predominant wavelength which activates cytochrome C oxidase.

The retaining of a youth appearance and/or healthy skin and/or hair is resulting in an unceasing search for novel compounds and/or for novel noninvasive treatment methods which make it possible to maintain or to improve the appearance of the skin and/or hair.

For some years, attention has been directed at aesthetic treatments employing light radiation of visible and/or infrared light, laser or LED type, and the like. The term used in particular is "photocosmetic treatment".

The use by dermatologists and beauticians of lasers and IPL (Intense Pulsed Light) to treat signs of skin aging, in particular wrinkles, is known in particular but these technologies are capable, under some conditions (high intensity and/or long treatment time) of causing damage to the dermis which can bring about erythema, oedema or pain.

The use of the LED (Light-Emitting Diode) is also known, which device specifically activates, for a given wavelength, cellular chromophores or acceptors in skin tissue and thereby initiates a cascade of biological metabolisms intended to revitalize/improve/regenerate/stimulate the working and the appearance of the skin.

Application WO2004/075985 describes in particular treatment methods employing light radiation defined in the visible and/or infrared region(s), optionally in combination with a photosensitizing active principle, for reducing wrinkles, rejuvenating the skin, promoting healing and repair of the tissues, or treating hypopigmentary disorders. A description is given of the repeated and controlled application in several stages of light radiation over periods of several hours.

The need remains to develop systems which are easy to employ and which do not exhibit skin damage capable of being generated by an excessive application (nature of the light source, intensity, duration) of light radiation.

It is this which the Applicant Company has managed to do by combining the administration of at least one cytochrome C oxidase substrate and/or one agent which increases the expression of the said substrate and of at least one light radiation exhibiting at least one predominant wavelength which activates cytochrome C oxidase.

This combination advantageously makes it possible to reduce the duration and/or the intensity of the light radiation administered while still being highly effective.

This is because the Applicant Company has discovered, surprisingly and unexpectedly, that the administration of a cytochrome C oxidase substrate in combination with a light radiation exhibiting at least one predominant wavelength ranging from 550 to 800 nm (emission spectrum of red light) results in an increased activity of this enzyme and makes it possible to ensure the satisfactory operation of the mitochondrial respiratory chain, to increase the production of energy and thus in particular to combat signs of cell aging and dehydration of the skin and/or hair. The satisfactory operation of the respiratory chain also makes it possible to ensure, in return, better protection against the detrimental change brought about by UV radiation.

Cytochrome C oxidase is present in the various cell types of the skin and hair.

It is known to be involved in the energy metabolism in the mitochondrial respiratory chain or redox chain which controls the energy level, the metabolism and the homeostasis of the cells.

This enzyme is a photoacceptor activated by red light: when photons are absorbed by the redox chain, they transfer their energy to the respiratory system resulting, via the change in electrochemical potential of the photoactivated cell and the transduction of intracellular signals mediated by $Ca^{2+}$ and AMPc, in a cascade of events in the cell (DNA and RNA synthesis, proliferative activity of the cells) and production of energy in the form of ATP.

This enzyme has the ability to catalyse the transfer of electrons to molecular oxygen in order to convert it into water molecules without forming intermediate free radicals harmful to the cell, according to the following scheme:

Scheme of the Reaction Resulting in the Production of ATP and of Water Molecules From Oxygen Cytochrome C, one of its substrates, is a small haem protein having an iron-comprising protoporphyrin IX catalytic site which is associated with the inner membrane of the mitochondrion. It is a soluble protein, unlike other cytochromes. It is an essential component of the respiratory chain. Cytochrome C is a highly conserved protein across the spectrum of species, found in plants, animals and many unicellular organisms. Analogues of it are known under the cytochrome names C1, C2 and C3.

Furthermore, it is known that the number of mutations at the level of the mitochondrial DNA of skin cells, in particular fibroblasts, increases with age, in particular in sequences encoding cytochrome oxidase (G. S. Gerhard et al., Mechanisms of Ageing and Development, 123, 2002, 155-166), having the effect of detrimentally affecting the production of energy and of reducing the overall metabolism of the cells of the skin.

UV radiation is also responsible for an increase in mutations at the level of the DNA of the mitochondrial genome, in particular in DNA sequences encoding proteins involved in the respiratory chain of the mitochondrion. The detrimental change in these proteins results in a reduction in the consumption of oxygen, a variation in the membrane potential, a reduction in the production of ATP and an increase in the synthesis of MMPs. These mechanisms are reflected in particular by a loss of hydration in the cells of the skin, a deterioration in the collagen and a reduction in the energy metabolism of the cells.

The combination according to the invention thus makes it possible to maintain the energy store (ATP) of the cells and production of water molecules so that all the cell functions are maintained.

The invention thus relates to the combination of at least one cytochrome C oxidase substrate and/or of at least one agent which increases the expression of the said substrate with at least one light radiation exhibiting at least one predominant wavelength which activates cytochrome C oxidase, in particular a light radiation exhibiting at least one predominant wavelength ranging from 550 to 1000 nm (the emission spectrum of red and/or infrared light), in a cosmetic treatment method and to a composition or a kit intended in particular to improve the appearance of the skin and/or hair.

The cytochrome C oxidase substrate and/or the agent which increases the expression of the said substrate can be formulated in a composition for administration by the topical route and/or by the oral route.

The light radiation exhibiting at least one predominant wavelength which activates cytochrome C oxidase can be in the form of a device or, according to one alternative, in the form of a compound capable of emitting and/or of specifically allowing to pass, in particular under exposure to light, a light radiation exhibiting at least one predominant wavelength which activates cytochrome C oxidase. In the latter case, the said compound which emits and/or filters the said light radiation which activates cytochrome C oxidase can be formulated in the same composition as the cytochrome C oxidase substrate and/or the agent which increases the expression of the said substrate or in a separate composition.

The invention thus relates in particular to a cosmetic method intended in particular to improve the appearance of the skin and/or hair comprising the simultaneous and/or sequential administration:
a) of at least one cytochrome C oxidase substrate and/or of at least one agent which increases the expression of the said substrate;
b) of at least one light radiation exhibiting at least one predominant wavelength which activates cytochrome C oxidase.

Advantageously, all the cosmetic methods according to the present invention are employed on subjects with healthy skin.

The term "light radiation exhibiting at least one predominant wavelength" is understood to mean, according to the invention, a light radiation distinct from white light comprising all the wavelengths of the spectrum.

This is because it is known that each wavelength has a specific target in the cells of the skin and/or hair, referred to as chromophore or photoacceptor.

Specifically, the Applicant Company has shown that certain wavelengths are capable of activating cytochrome C oxidase, whereas others have no effect, indeed even are capable of inhibiting it.

Preferably, the light radiation exhibits at least one predominant wavelength ranging from 550 to 1000 nm (emission spectrum of red light 550-800 nm and infrared light 800-1000 nm).

In particular, the light radiation exhibits at least one predominant wavelength ranging from 550 to 800 nm (emission spectrum of red light), in particular from 620 to 700 nm and more preferably still from 640 to 680 nm.

In particular, use will be made of a light radiation, the emission spectrum of which has an optimal peak in the vicinity of 660 nm, preferably in the vicinity of 660 nm +/−100 nm, in particular in the vicinity of 660 nm +/−40 nm and entirely preferably in the vicinity of 660 nm +/−15 nm.

According to a preferred form, the light radiation exhibiting at least one predominant wavelength which activates cytochrome C oxidase is applied to the skin and/or hair, in particular to the areas of skin and/or hair treated with a composition comprising at least one cytochrome C oxidase substrate and/or one agent which increases the expression of the said substrate, at a dose ranging from 0.01 to 200 J/cm², preferably from 0.1 to 30 J/cm².

The term "sequential" is understood to mean a successive (immediate) or delayed administration. In the case of a sequential administration, and advantageously, the cytochrome C oxidase substrate and/or the agent which increases the expression of the said substrate is/are administered before the administration of the light radiation exhibiting at least one predominant wavelength which activates cytochrome C oxidase but the said substrate and/or the said agent which increases the expression of the said substrate can also and complementarily be administered after a substrate+light radiation exhibiting at least one predominant wavelength which activates cytochrome C oxidase session.

According to a specific form, the light radiation exhibiting at least one predominant wavelength which activates cytochrome C oxidase is a compound which emits and/or filters, in particular under exposure to light or UV radiation, the said light radiation which activates cytochrome C oxidase; the said compound can be formulated in the composition comprising the said cytochrome C oxidase substrate and/or the said agent which increases the expression of the said substrate or else in another topical composition intended to be applied separately in time (before or after).

According to another form, use is made of a patch, in particular an iontophoretic patch, impregnated with at least one cytochrome C oxidase substrate and/or with an agent which increases the expression of the said substrate and provided with diodes which emit the said light radiation which activates cytochrome C oxidase.

The use of the method according to the invention can additionally comprise a stage, prior to or concomitant with the stages of the method according to the invention, targeted at improving the penetration of the said cytochrome C oxidase substrate and/or of an agent which increases the expression of the said substrate, for example while cooling the skin, by iontophoresis or by an occlusive system.

It is also possible to promote the penetration of the cytochrome C oxidase substrate and/or of an agent which increases the expression of the said substrate by carrying a chemical or mechanical peeling beforehand on the area to be treated.

Such a combination has the effect of ensuring the satisfactory operation of the mitochondrial respiratory chain and thus makes it possible to increase the production of energy and to combat in particular signs of cell aging and dehydration in the skin and/or hair.

The combination according to the invention thus makes it possible in particular to maintain and/or improve the energy metabolism of the cells of the skin and/or hair; to maintain and/or improve the hydration of the skin and/or hair; to maintain and/or improve the biomechanical properties of the skin (elasticity, firmness, tonicity); to prevent and/or treat signs of aging of the skin and/or hair; to improve the skin barrier function; to promote the regeneration of dermal and/or epidermal cells, in particular to prevent and/or improve the surface condition of areas affected by chapping and/or frostbite, related, for example, to a deficiency in cell oxygenation (ischemic cell situations caused in particular by cold and altitude).

According to a specific form, the method according to the invention is targeted at improving the hydration of the skin and/or hair.

According to another form, the method according to the invention is targeted at improving the skin barrier function.

According to yet another form, the method according to the invention is targeted at promoting the regeneration of dermal and/or epidermal cells, in particular improving the surface condition of areas affected by chapping and/or frostbite.

The method according to the invention is also targeted at preventing and/or combating signs of aging of the skin and/or hair.

In particular, the method according to the invention is targeted at alleviating visible or tactile irregularities in the surface of the skin, in particular alleviating wrinkles and fine lines, alleviating skin blemishes, reducing detrimental changes in the microrelief and/or smoothing the skin, prozmoting the regeneration of skin tissue, lightening the complexion and/or improving the lifeless appearance of the complexion, maintaining and/or improving the biomechanical properties of the skin (elasticity, firmness, tonicity), maintaining and/or improving the hydration of the skin and/or maintaining and/or improving the texture of the skin.

It is also targeted at preventing and/or treating hair loss, the slowing down in its growth, its greying, the reduction in the diameter of the hairs and the reduction in the vigour of the hairs.

Cytochrome C Oxidase Substrates and Agents Which Increase the Expression of the Said Substrate The term "cytochrome C oxidase substrate" is understood in particular to mean derivatives of compounds having an iron-comprising protoporphyrin IX site.

Mention may in particular be made, as examples according to the invention, of cytochrome C, its analogues, such as cytochrome C1, cytochrome C2 or cytochrome C3, and their mixtures.

According to a method of the invention, the cytochrome C oxidase substrate is chosen from cytochrome C, one of its analogues cytochrome C1, C2 or C3, and their mixtures.

Cytochrome C is sold in particular by Sigma, for example in a kit in which it is combined with a cytochrome C oxidase sold under the name Cytocox 1.

It is possible, as an alternative to the use of a cytochrome C oxidase substrate or to supplement it, to use an agent which increases the expression of the said cytochrome C oxidase substrate.

This alternative can be advantageous in responding to possible problems of formulation of the cytochrome C oxidase substrate.

The term "agent which increases the expression of the said cytochrome C oxidase substrate" is understood to mean any agent (or substance) capable of increasing the expression of the said cytochrome C oxidase substrate, in particular by activation of the protein synthesis of the cytochrome C oxidase substrate (in particular via regulation of the gene encoding the said substrate).

The term "agent which increases the expression of cytochrome C" is understood to mean any agent (or substance) capable of increasing the expression of cytochrome C, in particular by activation of the protein synthesis of cytochrome C (in particular via regulation of the gene encoding the protein cytochrome C).

Mention may be made, as agent which increases the expression of the said cytochrome C oxidase substrate, of an agent which increases the expression of cytochrome C.

Other agents which increase the expression of cytochrome C which can be used according to the invention can be selected by a person skilled in the art, for example in an in vitro test on human fibroblasts consisting in:
  incubating fibroblasts in a culture medium suited to their growth and their synthesis activities;
  bringing them into the presence or not (control) of a sufficient amount of the test compound, for example 0.1, 1 or 3%;
  measuring, by immunofluorescent labelling on a cell culture and/or by Western blotting using an antibody specific for cytochrome C, the expression of cytochrome C induced by the presence of the test compound;
  selecting the compounds for which an increase in the expression of cytochrome C with respect to the control, preferably an increase of more than 10%, indeed even of more than 20%, with respect to the control, is obtained, in particular when the compound is added at the concentration of 1% in the culture medium.

According to a first embodiment, the cytochrome C oxidase substrate and/or the agent which increases the expression of the said substrate is formulated in a composition intended for topical administration to the skin.

According to another embodiment, the cytochrome C oxidase substrate and/or the agent which increases the expression of the said substrate is formulated in a composition intended for oral administration.

It can also be advantageous to combine topical and oral administrations in order to optimize the desired effects.

The said cytochrome C oxidase substrate can be present in a composition according to the invention in a content, as active material, ranging from 0.000001 to 20% by weight, with respect to the total weight of the said composition.

The said cytochrome C oxidase substrate will generally be present in a composition of the invention in a content ranging from 0.001 to 20% by weight, with respect to the total weight of the said composition. Preferably, the content will range from 0.01 to 10% by weight and preferably from 0.01 to 1% by weight, with respect to the total weight of the said composition. Preferably, the said cytochrome C oxidase substrate will be present in a composition according to the invention in a content, as active material, ranging from 0.00001 to 2% and, entirely preferably, the said cytochrome C oxidase substrate will be present in a composition according to the invention in a content, as active material, ranging from 0.00002 to 0.1%.

The agent which increases the expression of the said cytochrome C oxidase substrate can be present in a composition according to the invention in a content, as active material, ranging from 0.000001 to 30% by weight, with respect to the total weight of the said composition.

The agent which increases the expression of the said cytochrome C oxidase substrate will generally be present in a composition of the invention in a content ranging from 0.001 to 30% by weight, with respect to the total weight of the said composition. Preferably, the content will range from 0.01 to 20% by weight and preferably from 0.01 to 5% by weight, with respect to the total weight of the said composition.

Preferably, the said agent which increases the expression of the said cytochrome C oxidase substrate will be present in a composition according to the invention in a content, as active material, ranging from 0.00001 to 2% and, entirely preferably, the said cytochrome C oxidase substrate will be present in a composition according to the invention in a content, as active material, ranging from 0.00002 to 2%.

The highest contents by weight are generally reserved for applications in the solid form (for example powder form) or patch form.

Light Radiation Which Activates Cytochrome C Oxidase

The term "light radiation which activates cytochrome C oxidase" is understood to mean the light radiation used under conditions (wavelength, intensity, exposure time) such that they can stimulate the enzymatic activity of cytochrome C oxidase in the presence of its substrate and/or of an agent which increases the expression of the said substrate and can in particular stimulate the following reaction resulting in production of energy (ATP) and of water molecules.

A light radiation which activates cytochrome C oxidase which can be used according to the invention can be selected according to an in vitro test, as described in Example 1 below, consisting in:

exposing or not exposing (control) cytochrome C oxidase and its substrate (cytochrome C) to light radiation of given wavelengths, for example at a dose of 2.7 joules, evaluating the effect of the said light radiation on the activity of the enzyme, with respect to a control, and selecting the light radiation capable of increasing the activity of the said enzyme, in particular of increasing the activity of the said enzyme by at least 10%, with respect to the control kept sheltered from the light.

Specifically, the Applicant Company has been able to show that, while a light radiation exhibiting at least one predominant wavelength corresponding to the emission spectrum of red light (dose 2.7 joules) is capable of activating cytochrome C oxidase (+33%), other wavelengths (for example green light in the vicinity of 535 nm and blue light in the vicinity of 447 nm) do not have an effect.

When light radiation is absorbed by a tissue, it delivers energy to the tissue, which itself reacts with the light radiation according to the wavelength, the intensity and the duration of exposure to the said light radiation.

The intensity of the light radiation used according to the invention preferably does not exceed 150 mW/cm$^2$ and is preferably greater than 0.01 mW/cm$^2$. This intensity range ensures an effectiveness of treatment over a reasonable period of time, without causing damage to the skin tissue treated.

The duration of exposure to the light radiation which activates cytochrome C oxidase will be defined, according to the intensity of the said radiation, so that the total energy delivered (dose) to the skin and/or hair is from 0.01 to 200 J/cm$^2$, preferably from 0.1 to 30 J/cm$^2$, more preferably from 1 to 30 J/cm$^2$, indeed even from 5 to 30 J/cm$^2$.

Energy (in joules)=Intensity (in watts)×Time (in seconds).

As nonlimiting example, the duration of exposure to a device emitting light radiation which activates cytochrome C oxidase can range from 20 min to 120 min, preferably from 30 min to 120 min and more preferably still from 60 min to 90 min.

According to the surface condition of the skin and/or hair to be treated and the effect desired, it may be advantageous to carry out several applications daily of the said light radiation which activates cytochrome C oxidase in combination with the cytochrome C oxidase substrate, or one application daily, indeed even one application weekly, for a period of time of one to several months.

According to a preferred form, the light radiation which activates cytochrome C oxidase will in particular be a light radiation exhibiting at least one predominant wavelength ranging from 550 to 1000 nm, preferably from 550 to 800 nm, in particular from 620 to 700 nm, and more preferably still from 640 to 680 nm, preferably used at a dose ranging from 0.01 to 200 J/cm$^2$, preferably from 0.1 to 30 J/cm$^2$, more preferably from 1 to 30 J/cm$^2$, indeed even from 5 to 30 J/cm$^2$.

According to a preferred form, the light radiation exhibiting at least one predominant wavelength which activates cytochrome C oxidase is thus applied to the skin and/or hair, in particular to the areas of skin and/or hair treated with the composition comprising at least one cytochrome C oxidase substrate and/or one agent which increases the expression of cytochrome C, at a dose ranging from 0.01 to 200 J/cm$^2$, preferably from 0.1 to 30 J/cm$^2$.

Use may in particular be made, as "light radiation exhibiting at least one predominant wavelength which activates cytochrome C oxidase" which can be used according to the invention, of:

a light radiation emitted by a device ("physical" source),
a light radiation emitted by a compound ("chemical/biological" source), and their mixtures.

Devices Emitting a Light Radiation Which Activates Cytochrome C Oxidase

According to a first embodiment of the invention, the light radiation exhibiting at least one predominant wavelength which activates cytochrome C oxidase is emitted by a device.

The said device can be chosen in particular from a device emitting white light in combination with a specific filter which allows the said radiation which activates cytochrome C oxidase to pass; lasers; IPL; LEDs; and their combinations.

In particular, the said device emits a light radiation exhibiting at least one predominant wavelength ranging from 550 to 1000 nm, in particular from 550 to 800 nm, and is chosen in particular from: lasers, IPL, LEDs; a device emitting white light in combination with a specific filter which allows at least one predominant wavelength ranging from 550 to 1000 nm to pass (emission spectrum of red and/or infrared light), and their combinations.

Mention may in particular be made, as devices emitting a light radiation which activates cytochrome C oxidase which can be used according to the invention, of:

white light, natural or artificial, in combination with a specific filter or a screening device which allows at least one predominant wavelength which activates cytochrome C oxidase (for example wavelength of the emission spectrum of red and/or infrared light) to pass: mention may in particular be made of arc lamps (for example xenon lamp) or incandescent lamps as examples of devices emitting artificial white light. The term "natural white light" is understood to mean daylight, which will be combined with a screening device which specifically allows predominantly a colour (for example red) which activates cytochrome C oxidase to pass.

lasers (for light amplification by the stimulated emission of radiation); this is a light source of very high intensity which is monochromatic. Unlike white light (photons of various wavelengths emitted randomly at different times and in different directions), the light radiation emitted by a laser is a light composed of photons emitted at the same time and in the same direction.

Three elements characterize lasers: the wavelength (A); the mode of emission: continuous (constant power delivered), pulsed (energy is delivered in pulses, the frequency and the power of which can be adjusted) and ultrapulsed (the pulses have a set duration and power but the power is considerable and the duration is extremely short); and the power: from a few mW to tens of thousands of watts.

IPL: Intense Pulsed Light

The fundamental difference between laser and IPL lies in the fact that IPL can deliver hundreds, indeed even thousands, of colours simultaneously, whereas the laser delivers only a single wavelength. These machines make it possible to choose the wavelength suited to the problem to be treated just by changing the filter. They are also referred to as "noncoherent light sources". Emission of light pulses of high overall intensity is concerned.

This technology can deliver a broad emission spectrum of wavelengths which are absorbed by multiple chromophores. Large surface areas can be treated simultaneously.

LEDs: Light-emitting diodes (photomodulation (LED, light-emitting diode, see "The newest medical breakthrough for skin renewal and shrinking pores (2004)").

LED: the LED generally emits low-intensity light of a few milliwatts; they are classified within the category of low-power lasers (power of 1 to a few tens of mW).

According to a preferred form, use will be made of devices of LED type.

Mention may in particular be made, as examples of devices of LED type emitting a light radiation which activates cytochrome C oxidase which are available commercially of:

a) devices capable of being used in particular in institutes for caring for the skin and/or hair, such as:
Omnilux™ system (633 nm) from Photo Therapeutics Ltd.;
Lumiphase™ system (660 nm) from Opusmed Inc.;
Lightwave system (630 nm and IR 880 nm) from Lightwave Technologies;
Delphia™ and HydroFacial™ (600-700 nm and IR 700-1000 nm) systems from Edge Systems Corp.;
RevitaLight system (625 nm; IR 940 nm) from Skincare Systems Inc.

b) devices capable of being used at home, such as those sold in particular on the Internet (specialist sites or sales sites, such as e-Bay); mention may be made, for example, of the Mini photon from Photo Rejuvenation.

The light radiation according to the invention is preferably substantially monochromatic (predominant wavelength) with a wavelength ranging from 550 to 1000 nm, preferably from 550 to 800 nm, in particular from 620 to 700 nm, more preferably still from 640 to 680 nm and better still in the vicinity of 660 nm.

According to a specific form, it can be advantageous to have a device sequentially emitting a green light radiation and a red or infrared light radiation, in order to complement the antiaging effects of either of these lights.

In this case, the treatment sessions with red light radiation will preferably be offset in time with respect to the treatment sessions with the green radiation, in order to avoid any interference between the effects of the different wavelengths.

The sequential application of two devices emitting at different wavelengths thus makes it possible to draw part of the benefits of each light without interference of one with the other.

Compounds Emitting a Light Radiation Which Activates Cytochrome C Oxidase

According to another embodiment of the invention or to supplement a device as described above, the light radiation exhibiting at least one predominant wavelength which activates cytochrome C oxidase is emitted by a compound chosen from metabolites or active principles emitting, in particular under exposure to light (visible, UV), such a predominant wavelength which activates cytochrome C oxidase, a compound which filters the light in order to specifically allow the said predominant wavelength which activates cytochrome C oxidase to pass, and their mixtures.

According to a preferred form, the said compound emits a light radiation exhibiting at least one predominant wavelength which activates cytochrome C oxidase ranging from 550 to 1000 nm, preferably from 550 to 800 nm, in particular from 620 to 700 nm and more preferably still from 640 to 680 nm.

According to a specific form, the said compound emits the said light radiation when it is exposed to light (visible, UV). This exposure to light can be an exposure to daylight ("natural" light) or an exposure to an artificial light employing a device. In particular, use will be made of a device emitting a white or coloured or UV light intended to excite the said compound in order to allow it to emit the said predominant wavelength (for example red).

The intensity of this exposure to light will be such that it makes it possible for the said compound to emit the said radiation which activates cytochrome C oxidase, in particular at a dose ranging from 0.01 to 200 J/cm$^2$, preferably from 0.1 to 30 J/cm$^2$, more preferably from 1 to 30 J/cm$^2$, indeed even from 5 to 30 J/cm$^2$.

According to another form, the said compound emits a light radiation without exposure to the light: this is the case with compounds having an exothermic reaction (thermoluminescence) or compounds having a chemoluminescence or bioluminescence reaction.

According to an alternative form, the said compound emits a light radiation, in particular of infrared type, via an exothermic or thermoluminescence reaction (release of heat), for example by dissolving $CaCl_2$ (calcium chloride), $ZnCl_2$ (zinc chloride) or $AlCl_3$ (aluminium chloride). This reaction can take place at the time of the application to the skin of an anhydrous composition comprising the said compound, the skin intrinsically comprising an amount of water sufficient to trigger the exothermic reaction.

According to another alternative form, the said compound emits a light radiation by a chemoluminescence or bioluminescence reaction.

Mention may in particular be made of the bioluminescence reaction of luciferin in the presence of the enzyme luciferase, of ATP, of a mineral (for example magnesium) and of dioxygen, which exists naturally in fireflies:

luciferin+ATP+$O_2$→oxyluciferin+AMP+$PP_i$+light

The compound can also be capable of filtering the light radiation which activates cytochrome C oxidase according to the invention when it is subjected to exposure to natural or artificial light.

These chromic phenomena and the corresponding compounds are described in particular in the reference work "Chromic Phenomena, Technological Applications of Colour Chemistry, Peter Bamfield, The Royal Society of Chemistry, 2001".

Metabolites and Active Principles Which Emit and/or Filter Red Light

These substances are more particularly metabolites or active principles which emit, in particular under exposure to light (visible, UV), light between 550 and 800 nm, preferably from 620 to 700 nm and more preferably still from 640 to 680 nm.

Mention may in particular be made of:
red-coloured anthocyanins; red pigments or dyes; iron (III) complexes;
phosphorescent substances;
fluorescent substances;
and their mixtures.

Mention may in particular be made, by way of examples, of red-coloured anthocyanins, such as carthamin, cyanidin, delphinidin, pelargonin and betanin; red polyphenols; lycopene; brazilein, annatto extract, madder, red pigments, iron (III) complexes and their mixtures.

Use will preferably be made of lycopene, delphinidin and their mixtures.

Mention may in particular be made, as red pigments, of carminic acid, laccaic acid, phycoerythrins (algae) and their mixtures.

Mention may in particular be made, as iron(III) complexes, of the complexes with salicylic acid and derivatives (salicylates), with antibacterials, such as octopirox, or with thiocyanate, and their mixtures.

Mention may in particular be made, as phosphorescent substances which can be excited under visible or UV light, of phosphorescent pigments.

The term "red phosphorescent pigments" is understood to mean the conventional phosphorescent pigments listed below but also any cosmetically acceptable substance which emits a phosphorescent red light radiation with a wavelength of between approximately 550 and 800 nm, preferably from 620 to 700 nm and more preferably still from 640 to 680 nm. The presence of phosphorescent pigments provides the composition with a continuous source of red light, the phosphorescence is activated by exposure to the UV radiation conventionally present in daylight and its effect lasts several hours.

Mention may in particular be made, as fluorescent substances which can be excited under visible, UV or near IR light, of fluorescent pigments, such as Nile red (excitation 552 nm/emission 636 nm); glycoconjugated or nonglycoconjugated porphyrin derivatives (excitation 420-440/emission 650-680 nm), and their mixtures.

In particular, the metabolites or active principles emitting light between 550 and 800 nm, in particular under exposure to light, can be chosen from red-coloured anthocyanins, such as carthamin, cyanidin, delphinidin, pelargonin or betanin; red-coloured polyphenols; lycopene; brazilein, annatto extract, madder, red pigments, complexes of iron(III) with salicylic acid, octopirox or thiocyanate, red phosphorescent substances, red fluorescent substances and their mixtures. Use will preferably be made of red-coloured anthocyanins and/or lycopene.

Other Compounds Which Filter Red Light

Use may also be made, alternatively and/or in combination with the compounds emitting a light radiation which activates cytochrome C oxidase described above, of compounds capable of filtering the light in order to specifically allow the light radiation which activates cytochrome C oxidase to pass.

Mention may be made, by way of example, of holographic pigments comprising a polymer matrix in which a volume hologram is recorded, which act as prisms and have the property, on choosing the appropriate refractive index, of emitting red light when they are illuminated with white light. These systems are described by the Applicant Company in Application FR 0758017.

The volume hologram converts the incident light into one or more beams having spatial and spectral dependencies which are a function of the parameters of the hologram.

An example of a volume hologram is the hologram of "Denisyuk" type, which is a reflection hologram which can be obtained in a holographic film using a single laser beam, acting both as object beam and as reference beam, as disclosed in Application EP 1 754 968 A2 and on the site http://www.smartholograms.com/site/sections/technology/creating-sensors/htm and in Application EP 1 369 681 A1 (see FIGS. 1a and 1b in particular), these publications being incorporated by reference.

These compounds which filter red light require exposure to natural or artificial light in order to specifically allow the light radiation which activates cytochrome C oxidase to pass.

These compounds which emit and/or filter the light radiation which activates cytochrome C oxidase can be used at concentrations sufficient to emit and/or ensure the passage of an amount of light radiation which activates cytochrome C oxidase.

The said compound emitting and/or filtering, in particular under exposure to light, a light radiation exhibiting at least one predominant wavelength which activates cytochrome C oxidase is present in at least one of the compositions employed in the method of the invention in a content ranging from 0.01 to 20% by weight, with respect to the total weight of the said composition, preferably from 0.1 to 10% by weight, with respect to the total weight of the said composition.

According to a first form, the said compound emitting and/or filtering, in particular under exposure to light, a light radiation exhibiting at least one predominant wavelength which activates cytochrome C oxidase is present in the composition comprising the said cytochrome C oxidase substrate and/or the agent which increases the expression of the said substrate.

According to an alternative form, the said compound emitting and/or filtering, in particular under exposure to light, a light radiation exhibiting at least one predominant wavelength which activates cytochrome C oxidase is present in a composition separate from the composition comprising the said cytochrome C oxidase substrate and/or the agent which increases the expression of the said substrate.

These compounds emitting and/or filtering the light radiation which activates cytochrome C oxidase are used in an amount sufficient to ensure a light emission flux from 0.1 to a few tens of mW.

A person skilled in the art will adjust the duration of exposure to this light radiation emitted by the said compound according to the characteristics of the said compound and the effect desired.

Purely by way of indication, the areas of skin and/or hair to be treated can receive a total energy (dose) delivered to the skin and/or hair ranging from 0.01 to 200 $J/cm^2$, preferably from 0.1 to 30 $J/cm^2$, more preferably from 1 to 30 $J/cm^2$, indeed even from 5 to 30 $J/cm^2$.

Examples of cytochrome C oxidase substrates are described above.

In particular, the cytochrome C oxidase substrate is chosen from cytochrome C, one of its analogues cytochrome C1, C2 or C3, and their mixtures.

According to a specific form, the cytochrome C oxidase substrate and/or the agent which increases the expression of the said substrate is formulated in a composition intended for topical administration to the skin.

According to another form, the cytochrome C oxidase substrate and/or the agent which increases the expression of the said substrate is formulated in a composition intended for oral administration.

Use will preferably be made of topical administration.

In particular, the said cytochrome C oxidase substrate is present in the composition in a content ranging from 0.001 to 20% by weight, with respect to the total weight of the said composition, and the agent which increases the expression of the said cytochrome C oxidase substrate is present in the composition preferably in a content ranging from 0.001 to 30% by weight, with respect to the total weight of the said composition.

A further subject-matter of the invention is a composition comprising, in a physiologically acceptable medium,
a) at least one cytochrome C oxidase substrate and/or one agent which increases the expression of the said substrate, and
b) at least one compound emitting and/or filtering, in particular under exposure to light, at least one light radiation exhibiting at least one predominant wavelength which activates cytochrome C oxidase.

The said compound emitting and/or filtering, in particular under exposure to light, a radiation exhibiting at least one predominant wavelength which activates cytochrome C oxidase is as defined above.

In particular, it can be chosen from metabolites and active principles emitting and/or filtering, in particular under exposure to light, a radiation with a predominant wavelength ranging from 550 to 800 nm, preferably from 620 to 700 nm and more preferably from 640 to 680 nm.

Mention may in particular be made, by way of examples, of red-coloured anthocyanins, such as carthamin, cyanidin, delphinidin, pelargonin or betanin; red-coloured polyphenols; lycopene; brazilein, annatto extract, madder, red pigments, complexes of iron(III) with salicylic acid, octopirox or thiocyanate, red phosphorescent substances, red fluorescent substances and their mixtures.

Use will preferably be made of red-coloured anthocyanins, lycopene and their mixtures.

In particular, the compound emitting and/or filtering, in particular under exposure to light, a light radiation exhibiting at least one predominant wavelength which activates cytochrome C oxidase is present in the composition in a content ranging from 0.01 to 20% by weight, with respect to the total weight of the said composition.

According to a preferred form, the cytochrome C oxidase substrate is chosen from cytochrome C, one of its analogues cytochrome C1, C2 or C3, and their mixtures.

In particular, the cytochrome C oxidase substrate and/or the agent which increases the expression of the said substrate is present in the composition in a content ranging from 0.001 to 30% by weight, with respect to the total weight of the said composition.

The composition can be a cosmetic or pharmaceutical composition.

It will preferably be a cosmetic composition.

According to a first embodiment, the composition is intended for topical application to the skin and/or hair.

According to another embodiment, the composition is intended for oral administration.

The composition can also comprise an agent which promotes the penetration of the said compounds, such as solvents, desquamating agents and their mixtures.

A person skilled in the art will take care that the choice of these additional ingredients is compatible with the application of a device emitting a light radiation which activates cytochrome C oxidase and does not detrimentally affect the desired properties.

A further subject-matter of the invention is a kit comprising:
a) a composition comprising at least one cytochrome C oxidase substrate and/or one agent which increases the expression of the said substrate and at least one compound capable of emitting and/or filtering a light radiation exhibiting at least one predominant wavelength which activates cytochrome C oxidase;
b) a first device which makes it possible for the said compound present in the first composition to emit and/or filter the said light radiation exhibiting at least one predominant wavelength which activates cytochrome C oxidase.

According to an alternative, the invention relates to a kit comprising:
a) a first composition comprising at least one cytochrome C oxidase substrate and/or one agent which increases the expression of the said substrate;
b) a second composition comprising at least one compound capable of emitting and/or filtering a light radiation exhibiting at least one predominant wavelength which activates cytochrome C oxidase;
c) optionally a first device which makes it possible for the said compound present in the second composition to emit and/or filter the said light radiation exhibiting at least one predominant wavelength which activates cytochrome C oxidase.

In the case of a compound capable of emitting the light radiation which activates cytochrome C oxidase, the first device excites the said compound so as to cause it to emit the said light radiation which activates cytochrome C oxidase.

The said first device can in particular be:
a device which emits a light radiation exhibiting wavelengths of visible, UV and/or near IR light,
a separate composition intended to be applied to the skin and/or hair comprising an additional compound necessary for the chemoluminescence, bioluminescence or thermoluminescence reaction with the said compound.

In particular, the first device can be a device which emits a light radiation exhibiting wavelengths of visible and/or UV light, according to the nature of the compound present in the second composition. The device can emit a light radiation chosen from white light, a coloured light and a UV light. Preferably, the light radiation will be visible light and in particular red light.

In the case of a compound capable of filtering the light radiation which activates cytochrome C oxidase, the first device is generally a light radiation which is filtered by the said compound to give a light radiation which activates cytochrome C oxidase.

According to a specific form, the kits described above can additionally comprise a second device emitting a light radiation exhibiting at least one predominant wavelength which activates cytochrome C oxidase.

The invention also relates to a kit comprising:
a) a composition comprising at least one cytochrome C oxidase substrate and/or one agent which increases the expression of the said substrate;
b) a device emitting a light radiation exhibiting at least one predominant wavelength which activates cytochrome C oxidase.

The device emitting a light radiation exhibiting at least one predominant wavelength which activates cytochrome C oxidase is chosen in particular from a device emitting white light in combination with a specific filter which allows the said light radiation which activates cytochrome C oxidase (in particular a light radiation exhibiting at least one predominant wavelength corresponding to the emission spectrum of red and/or infrared light) to pass, lasers, IPL, LEDs and their combinations.

The cytochrome C oxidase substrate and/or an agent which increases the expression of the said substrate are as described above.

Examples of compounds which emit and/or filter, in particular under exposure to light, a radiation exhibiting at least one predominant wavelength which activates cytochrome C oxidase are described above.

The kit according to the invention can be a cosmetic kit or a pharmaceutical kit.

Preferably, it will be a cosmetic kit.

The constituent compositions of these kits can be compositions intended for topical or oral administration.
Preferably, they will be compositions intended for topical administration.

Formulation

The compositions employed in the method, the composition or the kit according to the invention as described above are intended for topical and/or oral application.

The composition generally comprises a physiologically acceptable medium, that is to say a medium compatible with the skin and/or its superficial body growths. It is preferably a cosmetically acceptable medium, that is to say a medium which exhibits a pleasant smell, a pleasant colour and a pleasant feel and which does not cause unacceptable discomfort (smarting, red blotches, tightness) liable to dissuade the consumer from using this composition.

For oral administration, in particular in an "oral cosmetic", the composition can be provided in particular in the form of capsules, including hard gelatin capsules, tablets, including sugar-coated tablets, granules, chewing gum, gels, syrups to be taken orally or any other form known to a person skilled in the art.

Preferably, the composition is a topical composition.

The term "topical composition" is understood to mean a composition intended for local application to any surface area of the body, including the skin, the mucous or semi-mucous membranes, the scalp or the hair.

For topical application to the skin, the composition can have the form of an aqueous, aqueous/alcohol or oily solution which is optionally gelled, of an emulsion with a liquid or semi-liquid consistency of the milk type, obtained by dispersing a fatty phase in an aqueous phase (O/W) or vice versa (W/O), of a triple emulsion (W/O/W or O/W/O), of a suspension or emulsion with a soft, semi-solid or solid consistency of cream or gel type, of a liquid, pasty or solid anhydrous product, of microemulsions, of microcapsules, or microparticles, of a vesicular dispersion of ionic type (liposomes or oleosomes) and/or nonionic type (niosomes) and/or of a dispersion of minute spheres.

It is also possible to envisage a composition in the foam form or also in the spray or aerosol form then comprising a pressurized propellant, or also in the patch or impregnated pad form.

The composition can thus be provided in the form of a lotion, serum, milk, O/W or W/O cream, gel, ointment, salve, powder, balm, patch, impregnated pad, soap, bar or foam.

According to the area of the body targeted and the intensity of application desired, a person skilled in the art can choose from different composition forms:
a composition intended to remain applied to the skin even after the exposure to the light radiation exhibiting at least one predominant wavelength which activates cytochrome C oxidase; this composition can be a dispersion of the lotion or gel type, an emulsion with a liquid or semi-liquid consistency of the milk type, obtained by dispersing a fatty phase in an aqueous phase (O/W) or vice versa (W/O), a suspension or emulsion with a soft, semi-solid or solid consistency of the cream or gel type, a multiple emulsion (W/O/W or O/W/O), a microemulsion, a vesicular dispersion of ionic and/or nonionic type, or a wax/aqueous phase dispersion;
a composition which remains in contact with the skin only throughout the duration of the exposure to the said light radiation which activates cytochrome C oxidase, such as a mask, in the form of a cream which the user can specifically apply to the area to be treated and can then subsequently remove, or a patch impregnated with a substrate; in this administration form, the masks or patches have to be sufficiently transparent to allow the light which activates cytochrome C oxidase to pass through.

The invention will now be illustrated by the following nonlimiting examples.

EXAMPLE 1

Activation of Cytochrome C Oxidase by a Specific Light Radiation (Emission Spectrum of Red Light)

The following example measures the stimulating effect of a light radiation exhibiting a predominant wavelength ranging from 550 to 800 nm, in particular from 620 to 700 nm, on the activity of cytochrome C oxidase.
The exposure of this enzyme to the said light radiation stimulates the production of molecules of ATP and of water according to the following chemical reaction:

$$4CytC(Fe^{2+}) + O_2 + 4H+ \xrightarrow{CytC\ oxidase} 4CytC\ (Fe^{3+}) + 2H_2O$$
$$ADP + PO_4^{2-} \quad\quad ATP$$

Description of the Protocol

Figure 2:
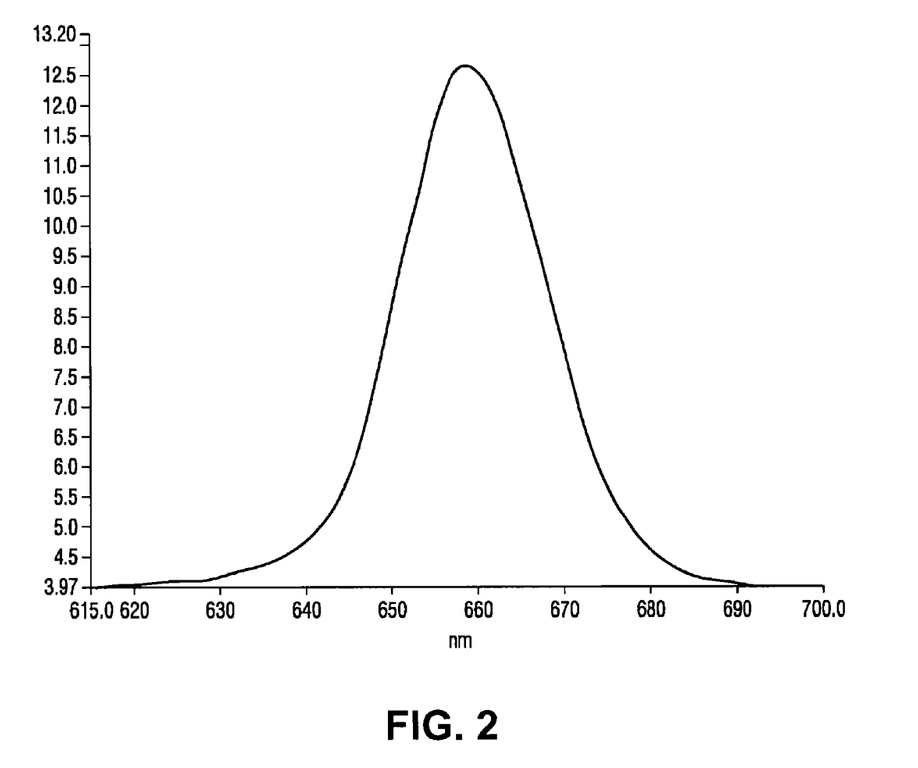
FIG. 2: red limit emission spectrum used in the examples.

General principle: the principle of these studies is to compare the activity of cytochrome C oxidase with or without prior exposure to a light radiation exhibiting a wavelength ranging from 620 to 700 nm.
Equipment and Reagents
  light source, with optical fibre (internal diameter 3 mm) and IL-1700 photometer +SED 033 probe (#6600): produces a light radiation, the emission spectrum of which is presented in FIG. 2;
  cytochrome C (0.22 mM) and cytochrome C oxidase (0.32 U/ml): Cytocox1 kit from Sigma.

Figure 1:
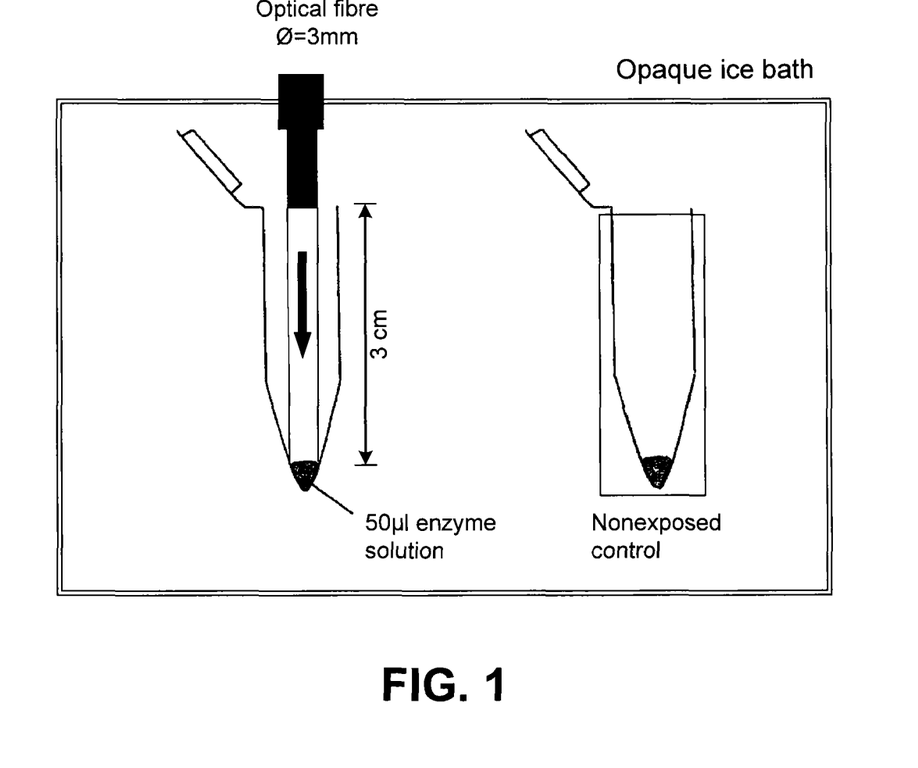
FIG. 1: set-up of the in vitro test on the activation of cytochrome C oxidase by red light.

The reduction of the protein takes place by addition of the 0.1M DTT (dithiothreitol) solution, i.e. a final concentration of 0.5 mM.
The absorbance is measured at 550 nm and at 565 nm: the A550/A565 ratio has to be between 10 and 20 (controls the conformity of the starting solutions).
Mode of Exposure of the Enzymes The enzyme (dehydrated powder form or enzyme solution) is placed in a conical Eppendorf tube. The amount is adjusted so that the enzymes in their entirety are subjected to the light radiation (wavelengths of between 620 and 700 nm) by an optical fibre with a diameter of 3 mm. Exposure to light is continuous and the energy provided by the light is 0.45 mW/cm$^2$ (see FIG. 1: set-up diagram, and FIG. 2: emission spectrum of the red light used in the tests).
The Eppendorf tubes are placed in an ice bath throughout the duration of the exposure in order to avoid an effect of the temperature. The control enzyme (not exposed to the said light radiation) is prepared at the same time and in the same way and is protected from the said light radiation by a backing which prevents external light from making a contribution (aluminium paper).
The cytochrome C oxidase is exposed to the light radiation (duration of 30 to 90 min), i.e. an equivalent dose of between 0.8 joule/cm$^2$ and 2.4 joule/cm$^2$, in solution at a concentration of 0.15 U/ml in a Tris-HCl, pH 7, buffer comprising 0.5 mM of sucrose.
After exposure, the cytochrome C oxidase is incubated with its substrate, ferrocytochrome C Fe$^{2+}$, in a mixture comprising 10 mM of Tris-HCl, pH 7, and 120 mM of KCl.
The activity of the enzyme is evaluated from the beginning of the reaction.

Measurement of Activity of the Enzyme

The absorption of cytochrome C at 550 nm varies with its oxidation state.
This property forms the basis of our measurement test. Cytochrome C is reduced with dithiothreitol and reoxidized with cytochrome C oxidase.
  125 µl are placed in Eppendorf tubes for the control and 125 µl are placed in Eppendorf tubes for the test sample. The test sample is then placed under light radiation for a duration of 90 minutes.
  The variation in the absorbance A550/min is then measured.
The enzymatic activity is then calculated according to the following formula:

$$U/ml=(dA/\min\times dil\times1.1)/(\text{vol of enzyme}\times21.84).$$

The light radiation emitting a predominant wavelength in the red significantly stimulates the activity of cytochrome C oxidase (+33%) for an irradiation time of 90 min, i.e. a dose equivalent to 2.4 joule/cm$^2$.

EXAMPLE 2

Formulation Examples

Compositions Combined with a Device

The formulations described below will be applied to the face or to the body immediately before prolonged exposure (30 min to 1 h 30) to a light radiation exhibiting at least one predominant wavelength ranging from 550 to 1000 nm, preferably from 620 to 700 nm. Use will be made, for example, of a device of Omnilux™ system type (633 nm) from Photo Therapeutics Ltd or a device of Lightwave™ system type (630 nm and 880 nm) from Opusmed Inc.

| Care cream for the skin: oil-in-water emulsion | |
|---|---|
| Ammonium polyacryldimethyltauramide (Hostacerin AMPS from Clariant) | 1.00% |
| Cyclohexasiloxane | 5.0% |
| Glycerol | 1.70% |
| Stearyl alcohol | 0.30% |
| Glyceryl stearate/PEG-100 stearate | 0.70% |
| Dimyristyl tartrate/cetearyl alcohol/C12-15 pareth-7/PPG-25 laureth-25 | 0.50% |
| Xanthan gum | 0.20% |
| Cytochrome C | 0.5% |
| Preservatives | 0.50% |
| Water | q.s. for 100 |

| Care cream for the skin: oil-in-water emulsion | |
|---|---|
| Ammonium polyacryldimethyltauramide (Hostacerin AMPS from Clariant) | 1.00% |
| Cyclohexasiloxane | 5.0% |
| Glycerol | 1.70% |
| Stearyl alcohol | 0.30% |
| Glyceryl stearate/PEG-100 stearate | 0.70% |
| Dimyristyl tartrate/cetearyl alcohol/C12-15 pareth-7/PPG-25 laureth-25 | 0.50% |
| Xanthan gum | 0.20% |
| Cytochrome C (as active material) | 0.0175% |
| Preservatives | 0.50% |
| Water | q.s. for 100 |

Iontophoretic Patch

According to another embodiment, a commercial reference patch Iontopatch™ (Travanti Pharma, Mendota Heights, Minn., USA) is applied to an area treated beforehand with one of the above creams.

It is subsequently connected to an electric current for delivering a galvanic current generated by a difference in potential of 1 V and comprising two electrodes, a Zn anode and an AgCl cathode, and is exposed to a light radiation exhibiting at least one predominant wavelength ranging from 550 to 1000 nm.

This treatment is carried out at the rate of once daily for 30 to 45 minutes.

Red mask (1)

Oily phase:

| | |
|---|---|
| Octyldodecanol | 6% |
| Apricot kernel oil | 6% |
| Triglycerides | 5% |
| Kaolin | 3% |
| Cetyl alcohol | 2% |
| Vitamin E acetate | 0.5% |
| Hydrogenated palm oil | 6% |
| Liquid fraction of shea butter | 5% |

Aqueous phase:

| | |
|---|---|
| Xanthan gum | 0.4% |
| Sucrose cocoate/sorbitan stearate (mixture sold by ICL under the name Arlaton 21121) | 5.5% |
| Glycerol | 3% |
| Dipyridamole | 0.30% |
| Ethanol | 5% |
| Cytochrome C | 0.1% |
| Delphinidin | 0.4% |
| Fragrance | 0.3% |
| Preservative | q.s. |
| Water | q.s. for 100 |

Red mask (2)

Oily phase:

| | |
|---|---|
| Octyldodecanol | 6% |
| Apricot kernel oil | 6% |
| Triglycerides | 5% |
| Kaolin | 3% |
| Cetyl alcohol | 2% |
| Vitamin E acetate | 0.5% |
| Hydrogenated palm oil | 6% |
| Liquid fraction of shea butter | 5% |

Aqueous phase:

| | |
|---|---|
| Xanthan gum | 0.4% |
| Sucrose cocoate/sorbitan stearate (mixture sold by ICL under the name Arlaton 21121) | 5.5% |
| Glycerol | 3% |
| Dipyridamole | 0.30% |
| Ethanol | 5% |
| Cytochrome C (as active material) | 0.00002% |
| Delphinidin | 0.4% |
| Fragrance | 0.3% |
| Preservative | q.s. |
| Water | q.s. for 100 |

The mask is applied to the areas of the skin to be treated and then the subject is placed under a source of white light (natural or electrical) for from 45 minutes to 1 hour.

The invention claimed is:

1. A method of improving the appearance of skin and/or hair, comprising:
   (a) administering at least one cytochrome C oxidase substrate and/or at least one agent which increases the expression of at least one cytochrome C substrate to the external skin and/or the hair of a subject; and
   (b) administering light radiation having a peak wavelength of 550 to 1000 nm, which activates cytochrome C oxidase, to cells in the external skin and/or the hair of the subject, wherein the light radiation is administered to cells in the external skin and/or hair of the subject at a dose of from 1 to 30 $J/cm^2$, wherein the light radiation exhibiting the peak wavelength which activates cytochrome C oxidase is emitted by at least one device selected from the group consisting of a device emitting white light in combination with a specific filter which allows the light radiation exhibiting the peak wavelength which activates cytochrome C oxidase to pass, lasers, intense pulsed light (IPL) source, and light emitting diodes (LEDs).

2. The method according to claim 1, wherein the light radiation exhibiting the peak wavelength which activates cytochrome C oxidase is administered to cells in the external skin and/or hair at a dose ranging from 5 to 30 $J/cm^2$.

3. The method according to claim 1, wherein the light radiation emitted by the device for activating cytochrome C oxidase has a peak wavelength of 620 to 700 nm.

4. The method according to claim 1, further comprising administering a compound to the external skin and/or the hair that emits light radiation exhibiting a peak wavelength ranging from 620 to 700 nm in response to receiving visible and/or ultraviolet light or filters visible and/or ultraviolet light to emit light radiation exhibiting a peak wavelength ranging from 620 to 700 nm, wherein the compound is at least one selected from the group consisting of red-coloured anthocyanin, polyphenol, lycopene, brazilein, annatto extract, madder, red pigment, a complex of iron(III) with salicylic acid, octopirox, thiocyanate, a red phosphorescent substance, and a red fluorescent substance.

5. The method according to claim 4, wherein the compound is present in a composition in a content ranging from 0.01 to 20% by weight, with respect to the total weight of the composition.

6. The method according to claim 4, wherein the compound is present in a composition which further comprises the cytochrome C oxidase substrate and/or at least one agent which increases the expression of the substrate.

7. The method according to claim 4, wherein the compound is present in a first composition and the cytochrome C oxidase substrate and/or at least one agent which increases the expression of the substrate is present in a second composition.

8. The method according to claim 1, wherein the cytochrome C oxidase substrate is at least one selected from the group consisting of cytochrome C, cytochrome C1, cytochrome C2 and cytochrome C3.

9. The method according to claim 1, wherein the cytochrome C oxidase substrate and/or the agent which increases the expression of the substrate is formulated in a composition suitable for topical administration to the skin.

10. The method according to claim 1, wherein the cytochrome C oxidase substrate is present in a composition in a content ranging from 0.001 to 20% by weight, with respect to the total weight of the composition.

11. The method according to claim 1, wherein the agent which increases the expression of the cytochrome C oxidase substrate is present in a composition in a content ranging from 0.001 to 30% by weight, with respect to the total weight of the composition.

12. The method according to claim 1, wherein the device is a device emitting white light in combination with a specific filter which allows the light radiation exhibiting the peak wavelength which activates cytochrome C oxidase to pass.

13. The method according to claim 1, wherein the device is a laser.

14. The method according to claim 1, wherein the device is an IPL source.

15. The method according to claim 1, wherein the device is a LED.

\* \* \* \* \*

UNITED STATES PATENT AND TRADEMARK OFFICE
CERTIFICATE OF CORRECTION

PATENT NO. : 9,827,311 B2
APPLICATION NO. : 14/802616
DATED : November 28, 2017
INVENTOR(S) : Julien Laboureau et al.

It is certified that error appears in the above-identified patent and that said Letters Patent is hereby corrected as shown below:

In the Claims

Column 20, Line 32, Claim 4, "620to 700" should read --620 to 700--;
    Line 35, Claim 4, "620to 700" should read --620 to 700--;
    Line 64, Claim 10, "0.001to 20%" should read --0.001 to 20%--.

Column 21, Line 2, Claim 11, "0.001to 30%" should read --0.001 to 30%--.

Signed and Sealed this
Third Day of April, 2018

Andrei Iancu
*Director of the United States Patent and Trademark Office*